(12) United States Patent
Cannon et al.

(10) Patent No.: US 10,820,893 B2
(45) Date of Patent: Nov. 3, 2020

(54) ENDOSCOPIC TRI-POINT BIOPSY NEEDLE

(71) Applicant: Cook Medical Technologies LLC, Bloomington, IN (US)

(72) Inventors: Aideen Cannon, County Galway (IE); Michael S. Clancy, County Limerick (IE); Aaron Collins, County Limerick (IE); Gerard Houlihan, County Limerick (IE); Kevin M. Chmura, Lewisville, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 252 days.

(21) Appl. No.: 15/884,659

(22) Filed: Jan. 31, 2018

(65) Prior Publication Data

US 2018/0228476 A1     Aug. 16, 2018

Related U.S. Application Data

(60) Provisional application No. 62/459,144, filed on Feb. 15, 2017.

(51) Int. Cl.
| | |
|---|---|
| *A61B 5/00* | (2006.01) |
| *A61B 10/04* | (2006.01) |
| *A61B 10/02* | (2006.01) |
| *A61B 17/3205* | (2006.01) |

(52) U.S. Cl.
CPC .......... *A61B 10/04* (2013.01); *A61B 10/0266* (2013.01); *A61B 10/0275* (2013.01); *A61B 17/32053* (2013.01); *A61B 2010/045* (2013.01)

(58) Field of Classification Search
CPC ............ A61B 10/0233; A61B 10/0266; A61B 10/0275; A61B 10/04

USPC .................................................. 600/564–567
See application file for complete search history.

(56) References Cited

U.S. PATENT DOCUMENTS

| | | |
|---|---|---|
| D300,060 S | 2/1989 | Molgaard-Nielsen |
| 5,477,862 A | 12/1995 | Haaga |
| 7,083,628 B2 | 8/2006 | Bachman |
| 7,189,206 B2 | 3/2007 | Quick et al. |

(Continued)

FOREIGN PATENT DOCUMENTS

| | | |
|---|---|---|
| WO | WO 2004/107984 | 12/2004 |
| WO | WO 2013/110079 | 7/2013 |
| WO | WO 2015/116954 | 8/2015 |

OTHER PUBLICATIONS

Springer, Andreas H. Mahnken, Jen Ricke, *CT- and MR-Guided Interventions in Radiology*, 1 pg., 2008.

(Continued)

*Primary Examiner* — Max F Hindenburg
(74) *Attorney, Agent, or Firm* — Brinks, Gilson & Lione

(57) ABSTRACT

A tri-point tissue-collection needle configured similarly to a fine-needle-aspiration needle is configured to excise intact tissue cores for collection. The distal tip is configured with three beveled points separated by cutting edges, where a single longer/more distal point is trailed by and circumferentially separated from a symmetrical pair of points, providing a bilaterally symmetrical needle cannula distal end. A stylet may be provided through a lumen of the needle during introduction into a patient body, where the distal end surface of the stylet may be configured to complement the tri-point needle end configuration.

20 Claims, 3 Drawing Sheets

(56) References Cited

U.S. PATENT DOCUMENTS

| | | | |
|---|---|---|---|
| 7,517,322 B2 | 4/2009 | Weikel, Jr. et al. | |
| 7,840,254 B2 | 11/2010 | Glossop | |
| 8,617,079 B2 | 12/2013 | Mitchell | |
| 8,764,782 B2 | 7/2014 | Akahoshi | |
| 8,961,550 B2 | 2/2015 | Lenker et al. | |
| 9,060,803 B2 | 6/2015 | Anderson et al. | |
| 9,101,350 B2 | 8/2015 | Stanley et al. | |
| 9,149,293 B2 | 10/2015 | Hardert et al. | |
| 9,332,970 B2 | 5/2016 | Beck et al. | |
| 10,159,470 B2* | 12/2018 | McWeeney | A61B 8/0841 |
| 2005/0101983 A1 | 5/2005 | Loshakove et al. | |
| 2006/0144548 A1 | 7/2006 | Beckman et al. | |
| 2011/0190660 A1 | 8/2011 | Levy | |
| 2011/0208089 A1 | 8/2011 | Sundheimer et al. | |
| 2011/0301620 A1 | 12/2011 | Di Betta et al. | |
| 2012/0010527 A1* | 1/2012 | Sundheimer | A61B 10/0233 600/566 |
| 2012/0059247 A1 | 3/2012 | Speeg et al. | |
| 2012/0130274 A1* | 5/2012 | Persat | A61B 10/0275 600/564 |
| 2012/0197157 A1 | 8/2012 | Ryan et al. | |
| 2013/0006145 A1* | 1/2013 | Toomey | A61B 10/0275 600/567 |
| 2013/0023918 A1 | 1/2013 | Morlet | |
| 2014/0243842 A1 | 8/2014 | Morlet | |
| 2014/0276205 A1* | 9/2014 | Miller | A61B 10/025 600/567 |
| 2014/0358028 A1 | 12/2014 | Vetter et al. | |
| 2015/0032140 A1 | 1/2015 | Khouri | |
| 2015/0201917 A1 | 7/2015 | Snow | |
| 2015/0342580 A1 | 12/2015 | Clancy | |
| 2016/0120517 A1* | 5/2016 | Almaatouq | A61B 10/0275 600/566 |
| 2017/0042567 A1* | 2/2017 | Begg | A61B 17/3417 |

OTHER PUBLICATIONS

Jason Zachary Moore, *Tissue Cutting in Needle Biopsy*, 103 pgs., 2011, University of Michigan.

Angiotech, *BioPince™ Ultra Full Core Biopsy Instrument*— Original 510(k), 5 pgs., Jun. 30, 2010.

Trudy D. Estridge, FDA U.S. Food and Drug Administration, *Protecting and Promoting Your Health*, 3 pgs., Jun. 30, 2016 https://www.accessdata.fda.gov/scripts/cdrh/cfdocs/cfpmn/pmn.cfm.

Pekato Inc. Medical Supplies, *BioPince Full Core Biopsy Instrument*, 3 pgs., Jun. 30, 2016, http://pekato.com/product/biopince.

Angiotech, *BioPince® Full-Core Biopsy Instruments*, 1 pg., undated, available as of Feb. 2017, www.pbn-medicals.com.

Angiotech, Biopsy *Instruments*, 2 pgs., Jun. 30, 2016 http://en.medical-bg.info/71/biopince.

Medical Technology & Gadgets Blog MedicalBuy.net; *BD Ultra-Fine Needle with PentaPoint for Less Pain During Insulin Injections*, 13 pgs., Jun. 29, 2016 http://medicalbuy.net/2012/09/bd-ultra-fine-needle-pentapoint-pain-insulin-injections.

Creganna *TACTX Medical, Partners from Idea to Reality*; 3 pgs., undated, available as of Feb. 2017, www.creganna.com.

University of MD Anderson Cancer Center, Brian R. Weston, MD and Manoop S. Bhutani, MD, FACG, FASGE, FACP, AGAF, *Optimizing Diagnostic Yield for EUS-Guided Sampling of Solid Pancreatic Lesions: A Technical Review*, 12 pgs., Jun. 2013, Gastroenterology & Hepatology vol. 9.

Cook Medical, *Needles for Biopsy and Special Purpose*, 36 Pgs., undated, available as of Feb. 2017, wwww.cookmedical.com.

*Cannula Point Styles*; 2 pgs., undated, available as of Feb. 2017, http://www.vitaneedle.com/cannula.htm.

\* cited by examiner

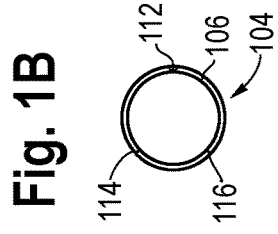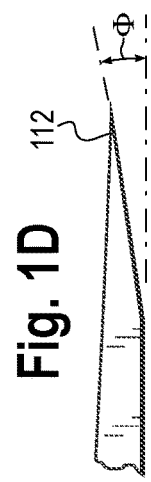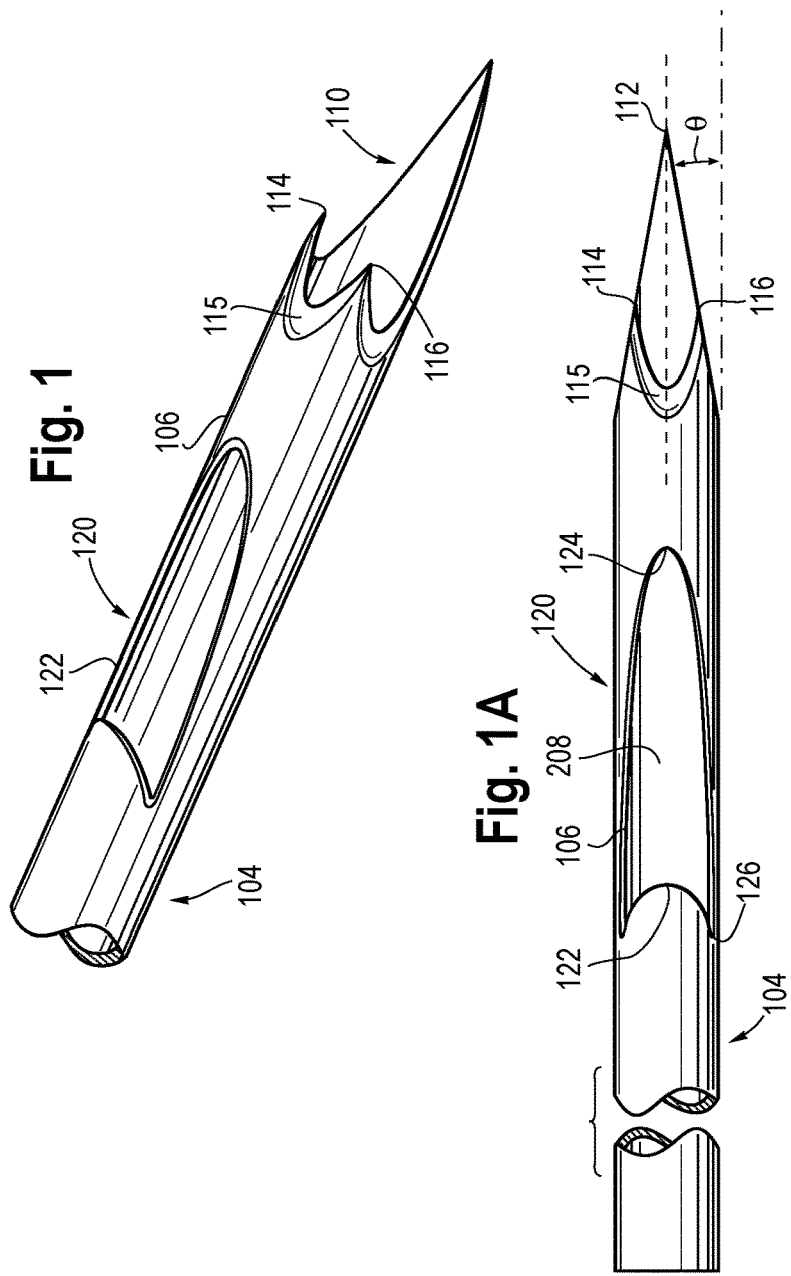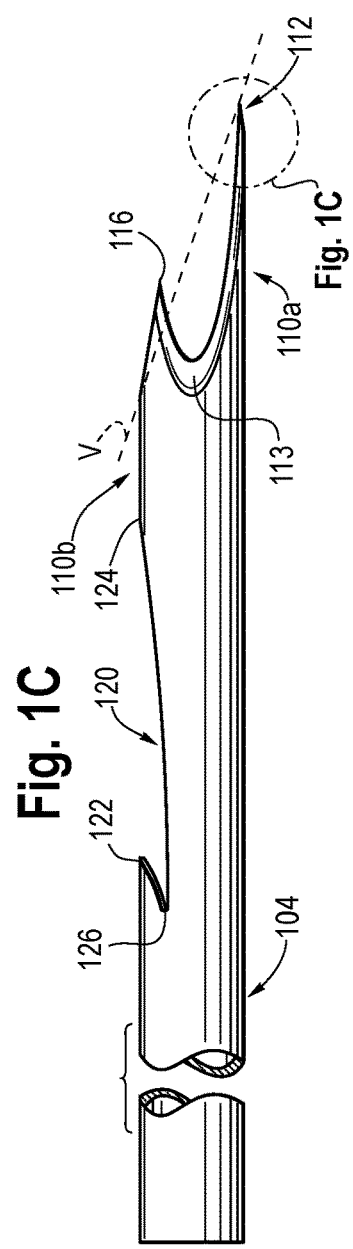

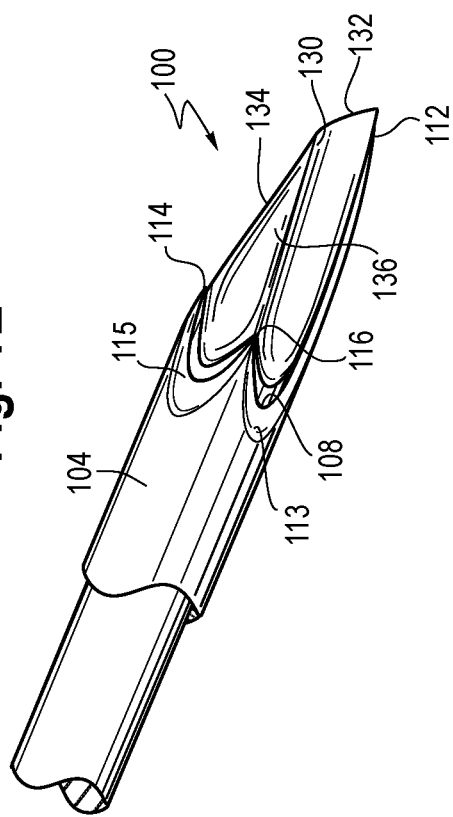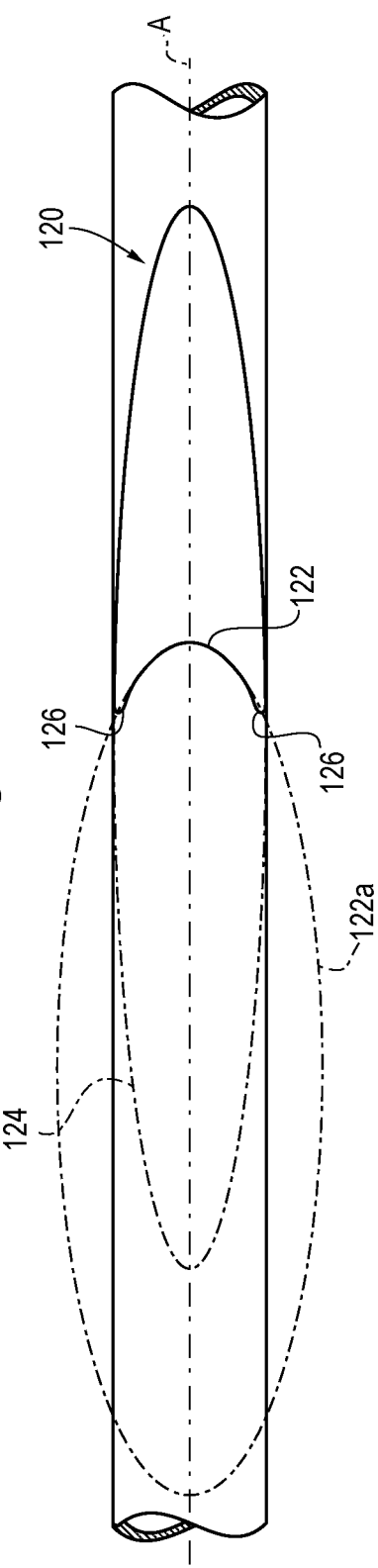

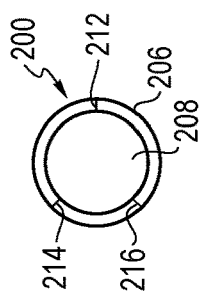
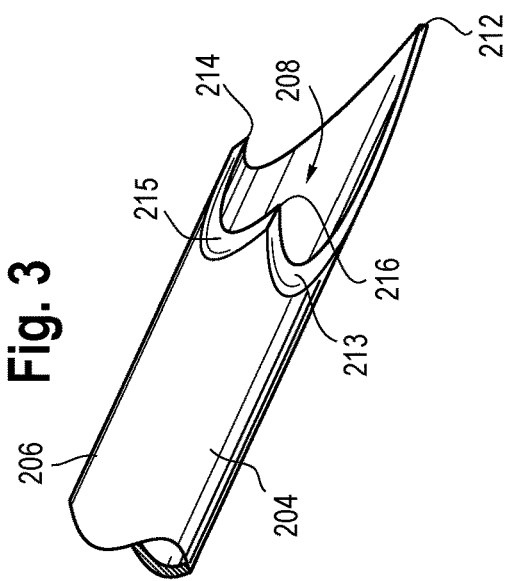
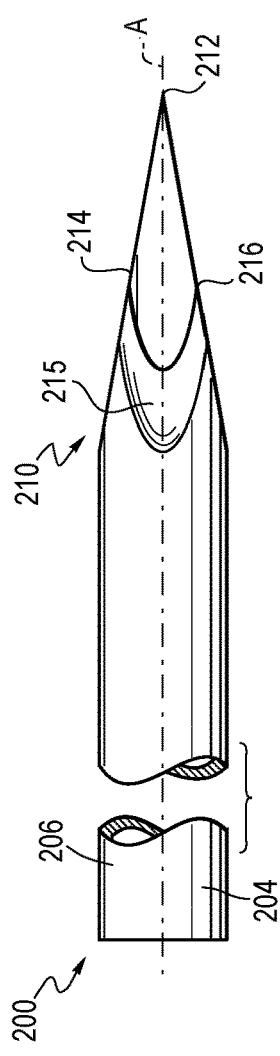
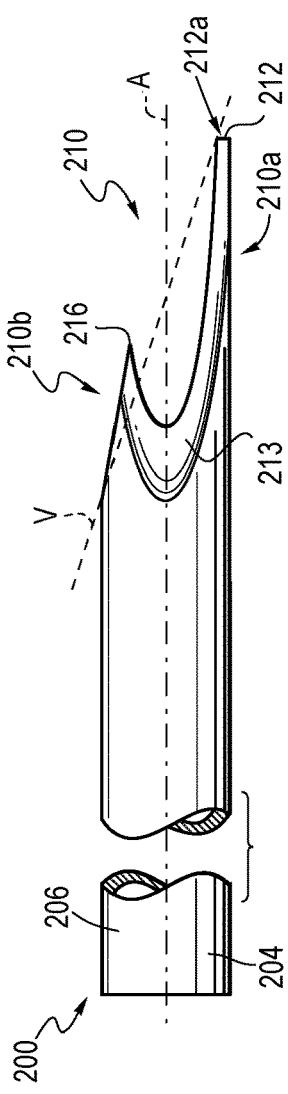
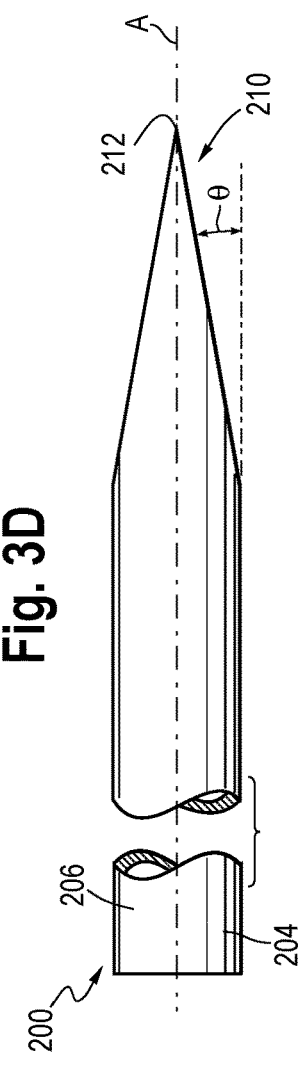

ENDOSCOPIC TRI-POINT BIOPSY NEEDLE

CROSS-REFERENCE TO RELATED APPLICATIONS

This application claims priority under 35 USC § 119 to U.S. Prov. Patent Application Ser. No. 62/459,144, filed Feb. 15, 2017, which is incorporated herein by reference in its entirety.

TECHNICAL FIELD

The invention relates generally to endoscopic surgical devices. More particularly, the invention pertains to a core biopsy needle configured for use during minimally-invasive procedures such as endoscopic tissue-collection procedures.

BACKGROUND

Liver biopsy is critically important for evaluating and directing treatment of patients who have liver disease. Although physicians rely heavily upon a patient's medical history, physical examination, radiographic imaging, and evaluation of serological markers important, diagnostic liver biopsy—particularly of histological-grade samples that have intact tissue with adjacent cells in their native conformation—is an important tool for diagnosis and/or therapeutic treatment planning. According to some of the medical literature, patient history, physical examination, and laboratory evaluation can miss significant fibrosis or cirrhosis in patients who do not undergo liver biopsy (e.g., where the patients have abnormal liver chemistries but no diagnostic serology data are available). Endoscopic ultrasound (EUS) fine needle aspiration (FNA) is a diagnostic biopsy procedure used to obtain a sample from a target site in a patient body. A fine needle (e.g., 18-gauge to 25-gauge) is directed to a target site, and suction is applied to the proximal end of a lumen of the needle to aspirate cells through its distal end. The procedure typically is far less invasive than other biopsy techniques, particularly those performed percutaneously (e.g., to sample a suspected breast tumor or subcutaneous lesion). Moreover, advances in endoscopic ultrasound (EUS) technology have helped physicians and patients by providing enhanced ability of a physician to visualize a biopsy needle to obtain a sample of material from a target site without requiring an open incision or use of large-bore needles and/or laparoscopic trocars.

Many current FNA techniques and needle devices typically obtain only a small number of cells useful for diagnostic evaluation. As a result, this technique includes a risk of false negatives where the few cells obtained in a sample do not accurately represent the presence of a tumor or other disease condition. The small sample size may also limit the diagnostic value of the procedure if the cells obtained are sufficiently few in number or sufficiently damaged during collection that they do not enable a definitive diagnosis. Accordingly it would be advantageous to provide a needle useful for EUS and/or percutaneous FNB (fine needle biopsy) that can obtain a larger sample size (e.g., a larger number of cells in the sample or a "tissue core" comprising intact adjacent cells held together in similar or identical form to their native location) without requiring a significantly larger-gauge needle or requiring multiple passes of the needle to reliably obtain a diagnostically efficacious sample with regard to the number and integrity of the cells in the sample, including particularly the number of intact cells in and integrity of the structure of a tissue core sample. Such needles, including for example the Cook ProCore® line of needles (available from Cook Medical, Bloomington, Ind.) have been demonstrated reliably to provide intact tissue cores when operated endoscopically, including in the head of the pancreas and other hard-to-access regions of patients' gastrointestinal anatomy. However, the type of tissue being sampled in the liver and other target areas, as well as the different path(s) for navigating endoscopically to a target site pose different performance challenges and therefore require different structure than the available needles.

Endoscopic ultrasound (EUS) has emerged as an essential diagnostic examination for the diagnosis and management of a wide range of gastrointestinal, hepatobiliary, and pancreatic diseases. Its ability to provide for targeted biopsy with limited adverse event risk makes EUS an excellent procedure to acquire liver tissue for evaluating focal hepatic lesions. EUS also allows staging in malignant conditions by offering the potential to obtain image-guided direct biopsies of possible metastatic liver lesions, which can significantly alter a physician's therapeutic recommendations. As such, liver histopathology is acknowledged to be an essential tool for the diagnosis of liver disease and for therapeutic management. Percutaneous liver biopsy long has been the standard approach for liver tissue acquisition, but known advantages of minimally invasive procedures make appealing the prospect of alternatives to percutaneous sampling. Existing minimally invasive liver technologies have not reached optimal performance with regard to sample size and integrity. It would be advantageous to provide a small-bore needle configured to provide intact tissue in minimally invasive liver biopsy procedures.

BRIEF SUMMARY

Embodiments of needles disclosed here address these problems of the current technology and present advantages over existing needles with regard to both structure and methods. In one aspect a tissue-sampling needle device may include an elongate tubular cannula with a cannula wall defining a cannula lumen, where the cannula lumen extends longitudinally through the cannula. The cannula may include a distal beveled end with a long side and a short side and a notch through the cannula wall that is open to the cannula lumen. When present, the notch preferably is disposed proximally adjacent to the beveled distal cannula end and is generally centered in longitudinal alignment with the long beveled end side and on the same side as the short beveled end side. Also, the notch may include a distal lip defined by a portion of the cannula wall, the distal lip being configured to extend distally from a proximal-most end of the notch such that a central distal lip portion is disposed distal of lip end portions that are continuous with generally longitudinal lateral sides of the notch, and to include a distal-facing cutting edge. The distal beveled tip may be substantially bilaterally symmetrical including two beveled distal terminal pointed tips substantially symmetrically disposed opposite of, and proximal from, a longer beveled terminal end tip defining the distalmost terminus of the cannula.

In another aspect, a notched aspiration biopsy needle disclosed herein may include a flexible elongate tubular cannula sized no larger than 18-gauge, with a cannula wall defining a cannula lumen configured to communicate with a proximal source of suction. The cannula lumen extends longitudinally through the cannula, a distal beveled end of the cannula including a long side and a short side, and the distal end structure includes two beveled distal terminal pointed tips symmetrically disposed opposite of, and proximal from, a longer beveled terminal end tip defining the distalmost terminus of the cannula.

In another aspect a notched tri-point endoscopic biopsy needle may include a flexible elongate tubular cannula sized no larger than 18-gauge, including a cannula wall defining a cannula lumen configured to communicate with a proximal source of suction; where the cannula lumen extends longitudinally through the cannula; a distal beveled end of the cannula with a long side including a single, longer extended tip defining the distalmost cannula terminus and a short side including a symmetrically disposed pair of distal-pointed tips; a notch through the cannula wall, open to the cannula lumen; where the notch is disposed proximally adjacent to the beveled distal cannula end and is generally centered in longitudinal alignment with the short beveled end and opposite the long beveled end; where the notch includes an edge defined by a distal-facing portion of the cannula wall, where the cutting edge is both longitudinally and radially arcuate such that a center-most portion of the cutting edge is more distally disposed than are lateral-end portions of the cutting edge.

In another aspect, a method of tissue collection may include providing an elongate needle, that includes a beveled distal end and a notch open into a needle lumen, wherein the notch is near the distal end and is disposed opposite an angled distal face of the beveled distal end, and with two beveled distal terminal pointed tips symmetrically disposed opposite of, and proximal from, a longer beveled terminal end tip defining the distalmost terminus of the cannula. The method may further include directing the distal end of the needle into a target site, applying suction to the needle lumen; and moving the needle proximally in a manner engaging the proximally-facing cutting edge with the target site such that a sample from the target site is collected into the needle lumen.

BRIEF DESCRIPTION OF THE DRAWINGS

In order to assist the understanding of embodiments of the invention, reference will now be made to the appended drawings, which are not necessarily drawn to scale or proportion (although certain drawings may be to scale), and in which like reference numerals generally refer to like elements. The drawings are provided by way of non-limiting example, and should not be construed as limiting the invention unless specifically identified as doing so.

FIG. 1 shows a top-right perspective view of a notched needle embodiment with a three-point distal tip that is bilaterally symmetrical along its longitudinal axis;

FIG. 1A shows a top plan view thereof;

FIG. 1B shows a distal perspective end-on view of the embodiment of FIG. 1A;

FIG. 1C shows a side elevation view thereof;

FIG. 1D shows a magnified/detail side elevation view of a distalmost edge/end bevel thereof, called out from FIG. 1C;

FIG. 1E shows a perspective view of a distal needle end, including a removably-inserted stylet the ends of which are shaped to match, complement, and continue from the immediately-adjacent contours of the needle cannula;

FIG. 2 shows a top plan view of the contours of a side notch of a needle embodiment of FIG. 1;

FIG. 3 shows a perspective view of an embodiment of a three-point distal needle tip that is bilaterally symmetrical along its longitudinal axis, including a different terminalmost tip than the embodiment of FIGS. 1-1D;

FIG. 3A shows a top plan view thereof;

FIG. 3B shows a distal perspective end-on view of the embodiment of FIG. 3A;

FIG. 3C shows a side elevation view thereof; and

FIG. 3D shows bottom plan view thereof.

DETAILED DESCRIPTION

As used herein, the term "proximal" refers to the handle-end of a device held by a user ("doctor end"), and the term "distal" refers to the opposite end ("patient end"). The term "surgical visualization device" refers to endoscopes including CCD, ultrasound, fiber optic, and CMOS devices, as well as other devices used for visualizing an internal portion of a patient body such as, for example, a laparoscope or bronchoscope. The term "tissue" (used alone and with regard to histological-grade samples) refers to a group of cells that are intact and that retain the same attachment/arrangement together as in the body from which they are harvested (in contrast with the disaggregated cellular material associated with cytological-grade samples, even though such material may be mixed in a sample collected by a needle device). As such, tissue is subject to histological staining and preservation techniques that preserve the native arrangement of adjacent cells with their internal and intervening structure. The term "bilaterally symmetrical" describes a property of the device embodiments disclosed herein where the cylindrically tubular distal cannula end has a single plane of symmetry, said plane extending through a central longitudinal axis of the cannula, a distalmost terminal end of the cannula, and equidistant between two distal-terminal end tips.

The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field of needle design), and should be interpreted to include at least any legal equivalents, minor but functionally-insignificant variants, standard manufacturing tolerances (unless otherwise specified by a given range/tolerance), and including at least mathematically significant figures (although not required to be as broad as the largest range thereof). In particular, the term "substantially" when applied to any form of "symmetrical" includes exact symmetry as well as minor variations, where the longest distal tip of the three tips is at least twice as long as a shortest one of the shorter tips, even if one of the shorter tips is a different longitudinal length than the other shorter tip (within about 70%-190% of the length said other shorter tip), and when used with reference to relative surface areas and/or volumes includes exact filling/matching as well as variances within normal manufacturing tolerances (e.g., for relative sizes of stylet OD and needle lumen ID). And, in certain preferred embodiments, the symmetry provides being at least very nearly symmetrical, where the longest distal tip of the three tips is at least 1.5× as long as a longer one of the shorter tips, even if one of the shorter tips is a different longitudinal length than the other shorter tip (within about 90%-180% of the length said other shorter tip).

Unless otherwise stated, the needle gauge sizes are to be interpreted as standard, including that the inner diameter and outer diameter are uniform along each needle embodiment unless otherwise specified. The term "coincident" is used herein to mean "having accordant characteristics" and specifically to refer to two or more lines or surfaces that are aligned with each other so as to present a continuous whole or that are so substantially parallel and/or aligned that they would appear to the naked human eye to be continuous or very nearly so. The term "bevel" used as a noun refers to a surface or line at a non-right-angle slant/inclination relative to another surface or line, while when used as an adjective refers to having the property of such a non-right-angle slant/inclination relative to another surface or line. Embodiments including the present needle tip construction may be configured for endoscopic use including a handle of the type described in US2013/0006144 to Clancy et al., which is incorporated herein by reference, with an elongate flexible needle having sufficient length and flexibility to extend through an endoscope (e.g., a duodenoscope accessing the biliary tree of a patient, an end-viewing endoscope, or any other type of endoscope).

One embodiment of a tri-point tissue-sampling needle device is described with reference to FIGS. 1-1D, which show different views of a distal length of a tissue-sampling needle device 100. Certain preferred embodiments will be constructed of sufficient length and flexibility for effective operation through a working channel of a peroral endoscope such as an end-viewing gastric endoscope or a duodenoscope into an abdominal cavity of a patient's body. For example, the needle's tubular cannula 104 may be constructed of 304 stainless steel or another surgical grade metal, and sized from 25 gauge to 18 gauge, and from about 50 to about 200 cm in length, with one preferred length of about 180 cm for use with certain endoscopes. Part or all of the leading distal end and edges of the needle cannula may be tipped and/or otherwise coated with titanium nitride (to improve edge retention and corrosion resistance while reducing insertion friction), e.g., as described in US2013/0006145 to Toomey, et al., which is incorporated herein by reference in its entirety. Those of skill in the art will appreciate that the construction specifications, dimensions, and flexibility of an endoscopic biopsy needle differ markedly from percutaneous biopsy needles in order to accommodate the operation of an endoscopic biopsy needle through an endoscope.

The device includes an elongate tubular cannula 104 that extends distally from a proximal end and handle assembly (not shown, but readily understood from well-known configurations in the art including by way of non-limiting examples the ProCore®, EchoTip® Ultra, and QuickCore® handles available from Cook Medical of Bloomington, Ind.). The cannula 104 includes a cannula wall 106 that defines a cannula lumen 108, through which a proximal suction source may communicate with the distal opening(s). A distal end region 110 of the cannula 104 is beveled where the major bevel of the distal tubular terminal end of the cannula 104 is defined along a leading edge (between tip 116 and the outer diameter longitudinal axis), adjacent line V-V shown in FIGS. 1A and 1C. This major bevel provides a long side 110a substantially parallel with the central longitudinal axis of the cannula 104 and extending to its distal-most tip end 112. A short side 110b of the beveled distal end 110 is opposite the long end 110a.

The short side 110b includes and terminates at two beveled distal terminal pointed tips 114, 116 symmetrically disposed opposite of, and proximal from, a longer beveled terminal end 112 that defines the distalmost terminus of the cannula 104. As illustrated in the drawing figures, the distal-terminal end surface of the needle cannula is also beveled across the thickness of the cannula wall 106, which trans-wall beveling is referred to herein as minor for the sake of distinguishing clarity, even while acknowledging in that the trans-wall beveling coincides with the "major" bevels that define the overall distal end contours of the needle cannula 104. In the illustrated embodiment of FIGS. 1-1D, beveling across a thickness of the cannula wall is angled from a thicker, more proximal, wall thickness to a thinner, more distal, wall thickness, while maintaining a constant, uniform inner diameter of the catheter lumen 108.

The major and minor beveling construction shown in this embodiment forms a parabolic minor-beveled region 115 between the pointed tips 114, 116 and also forms a matched/opposed pair of parabolic minor-beveled regions 113 between the distalmost terminus 112 and the pointed tips 114, 116. Each of the minor bevel regions 113, 115 includes a parabolic distal edge coincident with the cannula inner circumference defining the lumen 108, a parabolic proximal edge coincident with the cannula inner circumference, and a surface therebetween transiting the thickness of the cannula wall 106. In view of the cannula wall thickness, the parabolic distal edges of the minor bevel regions 113, 115 may be viewed as cutting edges that converge into penetrating points 112, 114, 116. This construction may further be understood with reference to the distal-end-on view of FIG. 1B, which shows the relative location of the distal-terminal tips 112, 114, 116 around the circumference of the needle cannula. The short-side terminal pointed tips 114, 116 are radially separated from each other by 90 degrees, and each of the tips is radially separated from the distal-most long side terminus by 135 degrees.

With reference to FIGS. 1A and 1C, both of which are drawn to scale, the minor and major beveling of this embodiment can further be understood by identification of the angles between the different parts. Each of the parabolic minor bevel faces is defined by a partial face of a cylinder oriented at about 10 degrees (±2°) relative to an axis defined along the outer longitudinal face of the cannula. As such the line V-V is oriented about 10 degrees from the central longitudinal axis and from the axis defined along the outer longitudinal face of the cannula, extending along the intrapoint region 115 to intersect the distalmost terminal point 112a of the distal end 112. Likewise, the leading, inner circumferential edges of the parabolic minor-beveled intertip regions 113 are—as viewed in the two-dimensional perspective of FIG. 1A—oriented about 10 degrees from the axis defined along the outer longitudinal face of the cannula. Because FIGS. 1A and 1C are drawn to scale, those of skill in the art will readily appreciate the configurations described herein, even where verbal descriptions may not fully and completely communicate every nuance of the distal end tri-point structure. Those of skill in the art will also appreciate that the contours illustrated for the tip of the needle embodiments (and for a complementarily configured stylet) may be provided in a number of different methods including laser cutting, grinding, precision casting, and other techniques. One technique may include providing a flat-ended cannula body with a stylet occupying its entire luminal cross section at the distal end, then applying a grinder to remove a partial cylinder of material from the top and sides at an angle providing the pointed tips and bevels illustrated in the presently-disclosed embodiments.

In the embodiment of FIGS. 1-1D, the distal-terminal cannula end 112 also includes a minor bevel at about 10 degrees to form a sharp distalmost point 112a coincident with the inner diameter/lumen surface of the cannula 104. FIG. 1D shows a magnified detail view of this distalmost bevel, which forms the distalmost tip 112a as the apex of a pyramid (where the luminal face may be slightly convex).

As shown in FIG. 1D, the minor bevel Φ across the thickness of the cannula wall 106 is about 9 degrees (±2°) from a longitudinal axis defined along the outer longitudinal face of the cannula 104.

This needle embodiment 100 includes a side notch 120 that is disposed proximally of, and adjacent to, the beveled distal cannula end 110 and that is generally centered radially on the short side 110*b*. In preferred embodiments, the notch 120 is generally arcuate, and—as shown with reference to FIG. 2—it can be represented from a top-down perspective as a first parabolic section 122 of a first ellipse 122*a* that is joined by a pair of lip end portions constructed as radiused transitions 126 to a second parabolic section 124 of a second ellipse 124 where the second ellipse intersects the first ellipse 122*a*. The parabolic edge 122 faces distally and descends (as viewed from the side in FIG. 1C) at an acute angle directly to the radiused transition curve 126. In one example embodiment of an 18 gauge needle with an outer diameter of about 0.05 inches the first ellipse 122*a* (an end of which is coincident with the parabolic distal-facing edge 122) may be about 0.098 inches wide and about 0.312 inches long, while the second ellipse 124 (a portion of which is coincident with and defines the distal and trailing/lateral sides of the notch 120) may be about 0.0565 inches wide and about 0.39 inches long.

In one example ("EXAMPLE 1"), the needle 100 may be an 18 gauge needle constructed with dimensions as follows: major and minor bevel angles provided as described above, where the minor bevel angle of the inter-point regions/faces 113, 115 is about 10 degrees, and the minor bevel angle defining the distalmost terminal tip 112 is about 9 degrees, where the longitudinal distance between the proximalmost/outer-circumferential end of the inter-short-points region 115 and the distalmost tip 112 is about 0.14 inches, the longitudinal notch length measured from the distalmost point of the proximal parabolic edge 122 to the distal notch end 124 is about 0.16 inches (and measured from the proximalmost notch end defined by the radiused transition 126 to the distal notch end is about 0.185 inches), the distance between the outer cannula circumference and a plane defining the deepest notch region is about 0.014 inches (such that the notch extends only about one-fourth to one-third in depth relative to the outer diameter but less than about one-half around the circumference), and the longitudinal distance measured from the distalmost point of the proximal parabolic edge 122 to the distal end 112 is about 0.36 inches. The major bevels defining the lateral edges of the distalmost terminal tip 112, designated Θ in FIG. 1A, (and the major bevel between tip 116 and the outer diameter longitudinal axis) each is about 10 degrees from a longitudinal axis of the outer needle diameter.

References to the distal end 112 and all other identified structures for measurement purposes should be understood as identifying a plane transverse to the central longitudinal needle axis (and therefore also to the above-noted longitudinal axes defined along the outer longitudinal face of the cannula) for purposes of defining longitudinal measurement. In other needle embodiments, such as a 18 gauge, 19 gauge, 20 gauge, 22 gauge, 25 gauge or other needle gauge, the absolute measurements will generally vary according to scale, while the angles—and particularly the angles defining the leading edges and points around the distal needle terminal end—will be identical or nearly identical to those defined above. This needle embodiment may also be constructed without the notch 120.

When operated—particularly in sampling liver tissue—the embodiments described here may present the same or lower puncture forces (with reference to user-perception metrics and/or mechanically-tested metrics) than other biopsy needles of the same gauge and will reliably acquire intact tissue samples with intact cores suitable for histological analysis and other diagnostic testing. During an operation for introducing a needle as presently disclosed, a stylet typically may be used to provide structural support—particularly for the tri-point distal tip, but then removed partially or completely from the cannula lumen before biopsy sample collection.

An elongate stylet 130 may be disposed removably through the cannula lumen 108. In preferred embodiments the stylet 130 will occupy substantially an entire cross-sectional area of at least a distalmost lengthwise portion of the cannula lumen 108. And, as shown in FIG. 1E, a distal end 132 of the stylet 130 will be beveled so that its surfaces align with the distal beveled cannula end surfaces in a substantially coplanar manner. This construction will provide enhanced support for the cannula (particularly during navigation to a target site) including providing a generally solid cutting and/or tissue-penetrating distal tip end formed by the matching major and minor bevels of the stylet 130 and the cannula 104. It should be appreciated that a rounded stylet end or other stylet end configuration may be practiced within the scope of the present invention.

Advantages regarding reduced insertion force of the current embodiments are currently understood to come from the tip configuration and beveling described (both with and without a complementarily beveled stylet), and advantages for sample acquisition efficacy are believed to rely at least in part on the leading/longer tip incising and stabilizing tissue while the shorter points and intervening sharp cutting edges slice through the tissue with minimal disruption of the tissue's integrity (when the stylet, if any, is removed for operation in tissue acquisition). The configuration shown in FIG. 1E can be manufactured by having a solid-cylindrical stylet body disposed in the needle lumen when the needle distal-end bevels are being ground, cut, or otherwise imposed upon the structure, so that the stylet fills or substantially fills the cross-sectional volume of the needle lumen and the stylet distal end includes beveled faces (e.g., negative cylindrical faces as shown) that align with and are co-planar/generally continuous with the distal needle bevels as illustrated. The distalmost stylet end may extend beyond the distalmost needle terminus, or the stylet and needle may be coterminal.

Stated differently, FIG. 1E shows the distal end of a needle cannula 104 with a stylet 130 having distal beveling, where the stylet 130 has a solid cylindrical body that occupies the entire cross-sectional volume of at least a distal length of the needle lumen 108 traversing the notch (in embodiments where a notch is present) and that distally terminates with concave/negative cylindrical faces that are exactly or nearly exactly coincident with the inter-tip faces 113, 115 of the minor bevels along the cannula's distal terminal end/edge. This results in providing an edge 134, 136 proceeding from each of the short side tips 114, 116 to converge at the distal stylet end 132.

FIGS. 3-3D show another embodiment of a tri-point tissue-sampling needle device 200. Certain preferred embodiments will be constructed of sufficient length and flexibility for effective operation through a working channel of a peroral endoscope such as an end-viewing gastric endoscope or a duodenoscope into an abdominal cavity of a patient's body. The dimensions and construction materials may be the same as or similar to those described for other embodiments herein.

This embodiment includes an elongate tubular cannula 204 extends distally. The cannula 204 includes a cannula wall 206 that defines a cannula lumen 208. A distal end region 210 of the cannula 204 is beveled where the major bevel of the distal tubular terminal end of the cannula 204 is defined a leading edge adjacent line V-V shown in FIG. 3C. This major bevel provides a long side 210a substantially parallel with the central longitudinal axis (A) of the cannula 204 and extending to its distal-most tip end 212. A short side 210b of the beveled distal end 210 is opposite the long end 210a.

The short side 210b includes and terminates at two beveled distal terminal pointed tips 214, 216 symmetrically disposed opposite of, and proximal from, a longer beveled terminal end 212 that defines the distalmost terminus of the cannula 204. As illustrated in the drawing figures, the distal-terminal end surface of the needle cannula at the pointed tips 214, 216 is also beveled across the thickness of the cannula wall 206, which trans-wall beveling is referred to herein as minor for the sake of distinguishing clarity, even while acknowledging in that the trans-wall beveling coincides with the "major" bevels that define the overall distal end contours of the needle cannula 204. In the illustrated embodiment of FIGS. 3-3D, beveling across a thickness of the cannula wall is angled from a thicker, more proximal, wall thickness to a thinner, more distal, wall thickness, while maintaining a constant, uniform inner diameter of the catheter lumen 208.

The major and minor beveling construction shown in this embodiment forms a parabolic minor-beveled region 215 between the pointed tips 214, 216 and also forms a matched/opposed pair of parabolic minor-beveled regions 213 between the distalmost terminus 212 and the pointed tips 214, 216. Each of the minor bevel regions 213, 215 includes a parabolic distal edge coincident with the cannula inner circumference defining the lumen 208, a parabolic proximal edge coincident with the cannula inner circumference, and a surface therebetween transiting the thickness of the cannula wall 206. This construction may further be understood with reference to the distal-end-on view of FIG. 3B, which shows the relative location of the distal-terminal pointed tips 214, 216 and the distal-most terminus 212 around the circumference of the needle cannula. The short-side terminal pointed tips 214, 216 are radially separated from each other by about 90 degrees (±2.5 degrees), and each of the tips is radially separated from the distal-most long side terminus 212 by about 135 degrees (as viewed from the distal end in FIG. 3B).

With reference to FIGS. 3A and 3B-3D, which are drawn to scale, the minor and major beveling of this embodiment can further be understood by identification of the angles between the different parts. Each of the parabolic minor bevel faces is defined by a partial face of a cylinder oriented at about 10 degrees (±2.5 degrees) relative to an axis defined along the outer longitudinal face of the cannula. As such the line V-V is oriented greater than 10 degrees from the central longitudinal axis ("line A" of FIG. 3C) and from the axis parallel thereto defined along the outer longitudinal face of the cannula, extending along the intra-point region 215 to intersect a distalmost terminal point 212a on the inner diameter/lumen surface of the distal end 112. Likewise, the leading, inner circumferential edges of the parabolic minor-beveled inter-tip regions 213 are—as viewed in the two-dimensional perspective of FIG. 3A—oriented about 10 degrees from an axis defined along the outer longitudinal face of the cannula and parallel with the central longitudinal axis when the needle is straight. Because FIGS. 3A and 3C-3D are drawn to scale, those of skill in the art will readily appreciate the configurations described herein, even where verbal descriptions may not fully and completely communicate every nuance of the distal end tri-point structure.

In the embodiment of FIGS. 3-3D, the distal-terminal end 212 is formed as a sharp distalmost wedge with a leading/distal-terminal edge 212a that is perpendicular to the longitudinal central axis and to the longitudinal axis defined by the outer surface of the cannula 204. FIGS. 3C and 3D show this distalmost bevel, which forms the distalmost tip/edge 212a as the peak/edge where the minor bevels coming down from the beveled inter-tip regions 213 intersect (where the luminal/inner diameter face may be slightly convex and the outer diameter face may be slightly convex). The other contrast with the embodiment of FIGS. 1-2 is that this embodiment does not have a notch, although it should be appreciated that either of the distal tip configurations can be provided in a needle with or without a notch, including a notch modified from the specific embodiment described with reference to FIGS. 1-2, and the feature of a sharp/tri-beveled distalmost point may be used in this and other embodiments as shown in FIGS. 1C-1D. Like "EXAMPLE 1," the embodiment described with reference to FIGS. 3-3D has been constructed and tested as "EXAMPLE 2," the dimensions of which are identical to "EXAMPLE 1," except that "EXAMPLE 2" does not include a notch nor is its distalmost tip beveled from its outermost surface to the surface of the lumen (in contrast with tip 112 of FIGS. 1C-1D, and embodying instead the configuration shown in FIG. 3C).

In another example, which has been constructed and tested ("EXAMPLE 3," which does not match exactly the scale of the drawings of FIGS. 3-3D, but is the same as those drawings other than as defined in this paragraph), the needle 200 may be an 18 gauge needle constructed with dimensions as follows: major and minor bevel angles defined as above, where the minor bevel angle of the inter-point regions/faces 213, 215 is about 10 degrees, where the longitudinal distance between the proximalmost/outer-circumferential end of the inter-short-points region 215 and the distalmost tip 212 is about 0.11 inches. In the EXAMPLE 3 embodiment, each of the major bevels defining the lateral edges of the distalmost terminal tip 212, designated Θ in FIG. 3D, is about 13 degrees (±2.5 degrees) from a longitudinal axis of the outer needle diameter that is parallel with the central longitudinal axis of the needle cannula. This example configuration provides a slightly shorter and therefore more robust tip than illustrated in FIGS. 3-3D.

A set of 18 gauge, 20 gauge, 22 gauge, and 25 gauge needles was constructed from 304 stainless steel according to the embodiments described above with reference to FIGS. 1-1D (including the specific dimensions identified in EXAMPLE 1), and FIGS. 3-3D (including the specific dimensions identified in EXAMPLE 2 and EXAMPLE 3) and was tested to evaluate objective and subjective puncture force, as well as efficacy in obtaining intact tissue cores from testing in animal tissue (via endoscopic sampling of live, sedated test animal liver tissue). One set of objective puncture force tests used an INSTRON® testing apparatus to measure the force in Newtons required to puncture a synthetic membrane simulating patient tissues. During user/physician testing by experienced, board-certified gastrointestinal endoscopists, each tester reported upon sensory perception of puncture force. The tester also evaluated and scored the samples collected with respect to the length and width of each tissue core, lack of fragmentation, and the number of portal triads obtained (Portal triad is defined as an intact segment of the tissue core from each sample—where the needle is introduced, reciprocated, and withdrawn, then the sample retrieved from the needle—containing at least one profile each of a portal vein, hepatic artery, and hepatic or bile duct). Surprisingly, the physicians testing the needles reported that their perception of puncture/insertion force required for the 18 gauge needle was the same as for the 20-gauge needle. This is surprising because instrument testing of those needles record a greater insertion force required for the larger 18 gauge needle, as expected due to the greater size and surface area contacting a membrane being punctured. Because the force required by a physician to use a given needle typically motivates them to use a smaller gauge, this presents an advantage not predicted: the 18 gauge needle embodiments provide a greater number of more-intact tissue cores with a greater number of portal triads as compared to a 20 gauge needle with the presently-disclosed novel tip and as compared with a currently-commercially-available 20 gauge needle with which its insertion/puncture force was evaluated as being the same (ECHO-HD-3-20-C from Cook Medical of Bloomington, Ind.).

When put into use for collecting a biopsy sample, the sample obtained preferably will include a desirable number of intact cells, preferably more intact cells (and more preferably an core of intact tissue) as compared with other biopsy needles ("more" indicating both a greater number and a higher degree of cell integrity within the sample obtained). It has been found that histological-grade fine needle biopsy intact tissue core samples may be obtained in this manner, which may be preferred for certain diagnostic purposes over samples obtained through other means. After sample acquisition into the needle lumen, the needle may be withdrawn from the patient's body.

In one preferred embodiment, during introduction of the device into a patient body, the needle cannula will be directed through the working channel of a peroral endoscope such as a duodenoscope into a patient's body. It is then navigated (under ultrasound visualization and/or fluoroscopy) into a target site. The needle device and methods disclosed here provide the advantages associated with FNA needles of small size and maneuverability, while offering a means of collecting more intact samples from target sites, and particularly from liver tissue. They also are not hampered by the guillotine-style moving parts of other notched needle systems known in the biopsy art (which are generally larger in scale due to a need for having an internal and/or external cutting member that movably transects the notch, which is expressly excluded from the present embodiments).

Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

We claim:
1. A tri-point tissue-sampling needle device, comprising:
   an elongate tubular cannula including a cannula wall defining a longitudinal cannula lumen constructed to receive a tissue sample;
   a distal beveled tubular terminal end of the cannula including a long side and a short side;
   where the short side includes two beveled distal-terminal pointed tips symmetrically disposed opposite of, and proximal from, a longer beveled terminal end tip defining a distalmost terminus of the cannula;
   where beveling across a thickness of the cannula wall is angled from a thicker, more proximal, wall thickness to a thinner, more distal, wall thickness between the two beveled points; and
   where the distal beveled tubular terminal end of the cannula is bilaterally symmetrical.

2. The device of claim 1, where the beveling across the thickness of the cannula wall provides a uniform inner diameter of the cannula lumen and provides an outer diameter that decreases proximally to distally.

3. The device of claim 1, further comprising a notch through the cannula wall, open to the cannula lumen;
   where the notch is disposed proximally of, and adjacent to, the beveled distal cannula end and is generally centered radially on the short side; and
   where a proximal end of the notch includes a distally-extending generally parabolic distal lip defined by a portion of the cannula wall, including a distal-facing edge that extends distally from a proximal-most end of the notch such that a central distal lip portion including the edge is disposed more distally than lip end portions that transition around a radiused curve from the lip to, and that are continuous with, generally longitudinal lateral sides formed by a parabolic distal boundary of the notch.

4. The device of claim 1, further comprising a solid stylet disposed through, and occupying substantially an entire cross-sectional area of, at least a lengthwise portion of the cannula lumen.

5. The device of claim 4, where a distal end of the stylet is beveled to align with the distal beveled cannula end tips.

6. The device of claim 1, comprising a first operating state for introducing the needle to a target, with said first operating state including a solid stylet disposed through, and occupying substantially an entire cross-sectional area of, at least a lengthwise portion of the cannula lumen, and a second operating state for collecting a sample with the stylet completely removed from the cannula lumen.

7. The device of claim 1, where a major bevel angle is inclusively between about 7.5 degrees and 15.5 degrees, said major bevel angle disposed between an edge leading to the longer beveled terminal end tip and a longitudinal axis along an outer diameter of the cannula, which longitudinal axis is parallel with a central longitudinal axis of the cannula.

8. The device of claim 7, where a first minor bevel angle is about 10 degrees across a complete thickness of the cannula wall between the two beveled distal terminal pointed tips and the longer beveled terminal end tip.

9. The device of claim 8, where a second minor bevel angle is about 9 degrees across a complete thickness of the cannula wall immediately adjacent of and extending proximally and radially externally from the longer beveled terminal end tip.

10. The device of claim 1, further comprising a solid stylet disposed through, and occupying substantially an entire cross-sectional area of, and an entire distal length, of the cannula lumen without extending substantially beyond a distalmost end terminus of the cannula.

11. The device of claim 1, wherein the cannula is configured as sufficiently flexible for passage through a working channel of a peroral surgical visualization device.

12. The device of claim 1, where the cannula comprises a selected one of a 18-gauge needle, 19-gauge needle, 20-gauge needle, 22-gauge needle, or 25-gauge needle.

13. The device of claim 1, where a major bevel angle is about 10 degrees between the longer beveled terminal end tip and a point on the cannula intermediate the two beveled distal terminal pointed tips, where a first minor bevel angle is about 10 degrees across a complete thickness of the cannula wall between the two beveled distal terminal pointed tips and the longer beveled terminal end tip, and where the longer beveled terminal end tip is configured as a wedge.

14. The device of claim 1, comprising a consistent inner diameter and outer diameter of the cannula along an entire length of the cannula lumen extending proximally from the distalmost end.

15. A notched tri-point endoscopic biopsy needle, comprising:
a flexible elongate tubular cannula sized no larger than 18-gauge, including a cannula wall defining a cannula lumen configured to communicate with a proximal source of suction;
wherein the cannula lumen extends longitudinally through the cannula;
a distal beveled end of the cannula with a long side including a single, longer extended tip defining a distalmost cannula terminus and a short side including a substantially symmetrically disposed pair of distal-pointed tips;
a notch through the cannula wall, open to the cannula lumen;
wherein the notch is disposed proximally adjacent to the beveled distal cannula end and is generally centered in longitudinal alignment with a short beveled end and opposite a long beveled end; and
wherein the notch includes a cutting edge defined by a distal-facing portion of the cannula wall, where the cutting edge is both longitudinally and radially arcuate such that a center-most portion of the cutting edge is more distally disposed than are lateral-end portions of the cutting edge.

16. The needle of claim 15, further comprising a stylet disposed through, and occupying substantially an entire cross-sectional area of, at least a distalmost lengthwise portion of the cannula lumen, and where a lateral side of the stylet fully obscures the notch when a distal end of stylet is distal of the notch.

17. A tri-point needle and stylet system comprising:
an elongate cylindrically tubular cannula with a cannula wall defining a coaxial longitudinal cannula lumen between a proximal end and a distal end of the cannula;
a solid stylet disposed removably through, and occupying substantially an entire cross-sectional area of, at least a distalmost lengthwise portion of the cannula lumen; and
where the distal end of the cannula and the distal end of the stylet include three coincident concave parabolic beveled surfaces converging at a common distalmost end terminus of the cannula and the stylet.

18. The system of claim 17, where the common distalmost end terminus of the cannula and the stylet coincide with a longitudinal axis along an inner diameter wall of the cannula lumen.

19. The system of claim 18, where each beveled surface is at an angle that is the same relative to a longitudinal axis along an outer diameter wall of the cannula lumen, which longitudinal axis bisects a proximalmost end of said beveled surface.

20. The system of claim 19, where the angle is about 10 degrees.

* * * * *